United States Patent [19]

Marion

[11] Patent Number: 4,673,384
[45] Date of Patent: Jun. 16, 1987

[54] VALVE FOR THE TREATMENT OF HYDROCEPHALUS

[75] Inventor: Bernard Marion, Montreuil sur Ille, France

[73] Assignee: Sophysa, Montreuil sur Ille, France

[21] Appl. No.: 851,326

[22] Filed: Apr. 14, 1986

[51] Int. Cl.$^4$ .......................... A61B 5/00; A61M 27/00
[52] U.S. Cl. ......................................................... 604/10
[58] Field of Search ........................................ 604/8–10

[56] References Cited

U.S. PATENT DOCUMENTS

| | | | |
|---|---|---|---|
| 3,886,948 | 6/1975 | Hakim ....................................... | 604/9 |
| 3,889,687 | 6/1975 | Harris et al. ............................ | 604/10 |
| 4,443,214 | 4/1984 | Marion ..................................... | 604/9 |

*Primary Examiner*—Dalton L. Truluck
*Attorney, Agent, or Firm*—Karl F. Ross; Herbert Dubno

[57] ABSTRACT

A subcutaneous valve is provided for the treatment of hydrocephalus adapted to be inserted between a ventricular catheter and a distal catheter. The valve comprises a body enclosing a chamber having formed through its cylindrical wall an inlet and outlet passage for cephalorachidian fluid. A rotor is journaled in the chamber for rotation about the chamber axis. A spring blade, fixed to the rotor extends arcuately along a cylindrical wall, bearing deflectably outwardly against a valve member and slides thereon to bias the member against a valve seat with a force depending on the angular position of the rotor and the chamber. The rotor is a disk in the form of a cut-out circular sector having a peripheral surface and two radial end surfaces. A stop means extends from a bottom wall of the chamber between the radial end surfaces of the rotor. The foregoing valve avoids the siphon effect when a patient moves between vertical and horizontal positions and is easily calibrated at any desired closing pressure for implantation.

3 Claims, 2 Drawing Figures

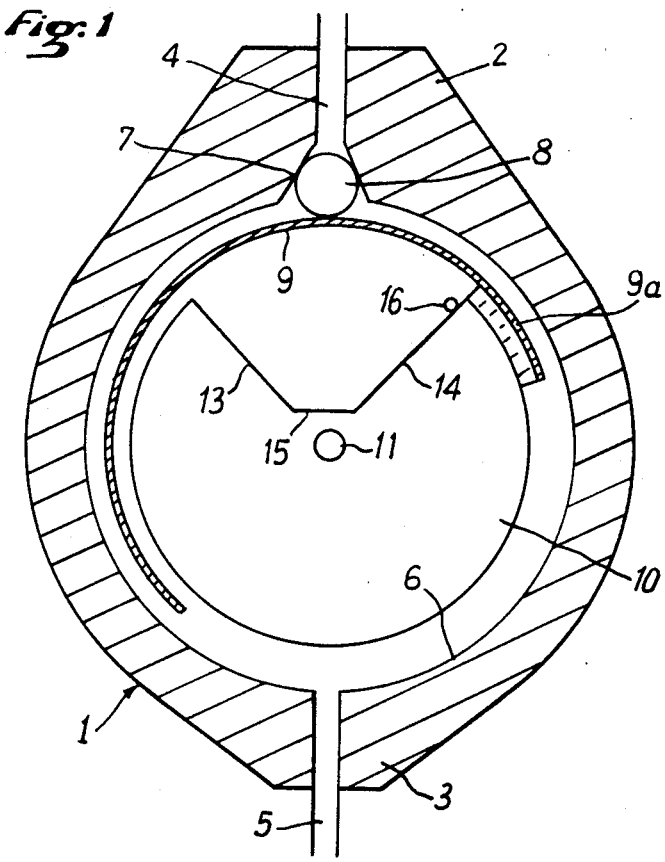
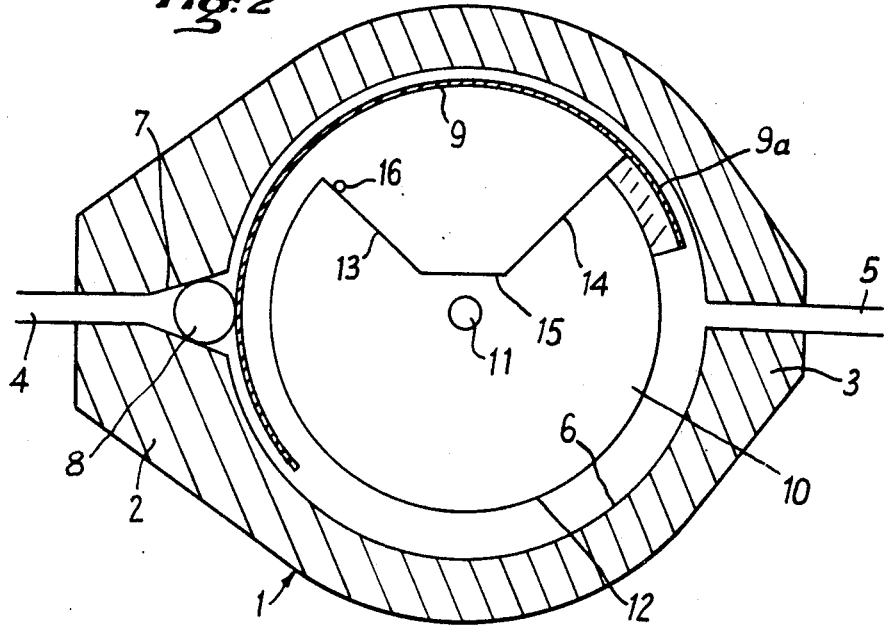

VALVE FOR THE TREATMENT OF HYDROCEPHALUS

BACKGROUND OF THE INVENTION

1. Field of the Invention

The present invention relates to a valve for the treatment of hydrocephalus.

It is known that hydrocephalus is a pathological state resulting in an abnormal increase of cerebrospinal fluid (CSF) into the ventricles of the brain. Most of the time hydrocephalus arises from an obstruction in the sites of absorption of the CSF, usually referred to as arachnoid villi which are the natural pathways of the CSF into the venous blood. Such obstruction, if not treated, results in an enlarged head in infants whose cranial sutures have not yet fused, with subsequent brain damage. In adults, because of the rigidity of the skull, the brain is subjected to an increased stress under the CSF pressure, and symptoms of headache, gait disturbance and dementia are reported.

The treatment of choice of hydrocephalus consists in diverting the cerebrospinal fluid contained in the ventricles of the cranial cavity towards any other absorptive area such as the heart or the peritoneum.

Usual procedures consist in introducing a catheter into the ventricles through a burr hole made into the skull, this catheter being connected to a shunt pressure valve inserted under the scalp, said valve being connected to another catheter leading subcutaneously either to the heart or to the peritoneum.

Therefore the assembly comprises an upstream catheter and a downstream catheter, but in fact it constitutes a unitary system which must be connected once or twice, according to the particular model utilized. The shunt assembly from its proximal end to its distal end is completely subcutaneous, thus affording a certain freedom of movement to the patient and avoiding infections.

Consequently, when a system for diverting the cerebro-spinal fluid is implanted in a patient, an adequate valve system must be inserted therein.

The valve is placed either at the end of the systems and is therefore referred to as a distal valve, or is placed near the burr hole and in this case is referred to as a proximal valve.

2. The Prior Art

A number of valve types have already been proposed up to now for such shunting systems used in the treatment of hydrocephalus.

The applicant's prior U.S. Pat. No. 4 443 214 discloses a valve adapted to be inserted between a ventricular catheter and a draining catheter comprising a body of flattened cylindrical shape enclosing a chamber having formed through its cylindrical wall an inlet passage for introducing the cephalorachidian fluid and an outlet passage for discharging this fluid. At the inner end of the inlet passage is a frustoconical seat engageable by a ball valve acting as a non-return valve. This ball valve is urged against the seat by a curved spring blade extending along the lateral inner wall of the chamber and mounted preferably in overhanging relationship on a diameter bar of magnetic material mounted in turn for concentric rotation on a pivot pin extending across the chamber. A tooth carried by the bar end opposite the spring blade is adapted to engage detent-positioning dents formed in the lateral wall of the chamber.

The advantage of such a valve is to give to a neurosurgeon the possibility of adapting externally and thus non invasively, the pressure of the valve to the condition of a patient according to the evaluation of the size of the ventricles and/or the measurement of the intracranial pressure.

However there is a category of patients who have already been implanted with a valve and who are reported to have a "siphon effect" consisting in a sharp negativation of their intracranial pressure everytime they stand up. Most of the time the valve that has been implanted originally was either of a low pressure gradient, and/or of a low resistance type. In such case the diversion of the CSF is made exclusively through the valve and the patient has become "shunt dependant". It may be also considered that some patients have no more distal resistance at the outlet of their catheter (peritoneal) and then, there is no damper effect when standing up, the so-called "siphon effect" becoming immediate and maximal in such cases.

When symptoms of severe syphon effect are reported to neurosurgeon, a revision of the implanted valve by a valve of a higher gradient is performed. However the closing pressure remains high even in the horizontal position, and there is no adjustment of the counter pressure of the valve according to the various positions of the patient's body.

OBJECT OF THE INVENTION

It is the primary object of the present invention to avoid the inconveniences characterizing the valves of the prior art by providing a valve which avoids the siphon effect when the patient moves between vertical and horizontal positions, the valve being easily calibrated at any desired closing pressure before implantation.

SUMMARY OF THE INVENTION

The subcutaneous valve of this invention for the treatment of hydrocephalous is adapted to be inserted and connected between a ventricular catheter and a distal catheter, said valve comprising a valve body formed with a cylindrical chamber having a cylindrical wall and a bottom wall.

An inlet is formed in the cylindrical wall which is connectable to the ventricular catheter. An outlet is formed in the cylindrical wall which opens into the chamber and is connectable to the draining catheter;

Means are provided for forming a valve seat at the inlet.

A valve member is juxtaposed with the valve seat and is engageable therewith to block flow from the chamber to the ventricular catheter but is diplaceable away from the valve seat to permit flow from the ventricular catheter into the chamber.

A rotor is journaled in the chamber for rotation about the axis of the chamber.

A spring blade is fixed to the rotor, extending arcuately along the wall and bears deflectably outwardly against the valve member and slides thereon to bias the valve member against the valve seat with a force which is a function of the angular position of the rotor in the chamber. The rotor is a disk in the form of a circular sector extending over at least about 180° and, preferably, over about 270° and has a peripheral surface and two radial end surfaces.

A stop means is provided which extends from the bottom wall of the chamber between the radial end surfaces of said rotor.

In a preferred embodiment the spring extends along at least one half of the periphery of said chamber and is fixed to said peripheral surface of said rotor adjacent to one of the radial surfaces thereof.

Other features of the invention will appear from the following description of a typical form of embodiment of the invention, given by way of example and illustrated in the attached drawing.

BRIEF DESCRIPTION OF THE DRAWING

FIG. 1 is an axial section of a valve according to this invention, shown in the position of a standing patient and;

FIG. 2 is a view similar to FIG. 1 in the position of a lying patient.

DESCRIPTION OF THE PREFERRED EMBODIMENT

The valve illustrated in FIG. 1 comprises essentially a valve body 1 of flat cylindrical form, made of a suitable plastic material.

Formed on this valve body 1 are two diametrally opposed projections 2 and 3 in which an inlet passage 4 and an outlet passage 5 for the cephalo-rachidian fluid are formed, respectively. These passages 4 and 5 open into the lateral cylindrical inner wall of a chamber 6 of a shape corresponding to that of said cylindrical body 1.

At the inner end of the fluid inlet passage 5 a frusto-conical valve seat 7 is provided for engagement by a corresponding ball valve 8. If desired, this seat 7 may be adjustable in its axial direction.

The ball valve 8 is normally urged against its seat 7 by a curved spring blade 9 extending along one portion of the lateral cylindrical inner wall of chamber 7. This spring 9 may advantageously extend over about one-half of the circumference of said chamber 6.

A rotor 10 is journaled in said chamber on a pin 11 extending from the bottom wall of said chamber at the center thereof.

The rotor 10 is a disk in the form of a circular sector extending over about 270° and having a peripheral surface 12 and two radial end surfaces 13 and 14 connected by a surface 15.

The spring 9 is fixed by an end thereof 9a to the peripheral surface 12 of the rotor 10 adjacent to the radial end surface 14.

As seen in the drawing stop means in the form of a stud 16 upstanding from the bottom wall of the chamber are provided to define two end positions of the rotor 10 with respect to the chamber and thus of the spring 9 with respect to the ball valve 8. In the position shown in FIG. 1 corresponding to a standing patient, the rotor 10 contacts the stud 16 by its end surface 14 whereas in the position of FIG. 2 corresponding to a lying patient said rotor 10 contacts the stud 16 by its other end surface 13. Due to gravity the axis of the rotor 10 remains vertical.

The position of the stud 16 with respect to the ball valve 8 and the length of the spring 9 are preset at manufacture stage in order to obtain in the end positions shown respectively in FIG. 1 and FIG. 2 predetermined resistant moments of the spring 9 on the ball valve 8 corresponding for instance to a fluid counter-pressure of 250 mm $H_2O$ in the vertical position of FIG. 1 and 30 to 40 mm $H_2O$ in the horizontal position of FIG. 2.

During the displacement of the patient between the vertical and horizontal positions, the counter-pressure changes proportionally to the position of the body, the response of the spring being immediate.

Of course, the device shown in the drawing is coated with, or embedded in, a protective material consistent with the human tissues, for example, a suitable silicone elastomer (not shown). This device is connected on the one hand to a conventional upstream drain coupled to a ventricular catheter, and on the other hand to a distal downstream drain or draining catheter.

What is claimed as new is:

1. In a subcutaneous valve for the treatment of hydrocephalus adapted to be inserted and connected between a ventricular catheter and a distal catheter, said valve comprising:

a valve body formed with a cylindrical chamber having a cylindrical wall and a bottom wall;

an inlet formed in said cylindrical wall and connectable to said ventricular catheter, an outlet formed in said cylindrical wall opening into said chamber and connectable to said draining catheter;

means forming a valve seat at said inlet;

a valve member juxtaposed with said valve seat and engageable therewith to block flow from said chamber to said ventricular catheter but displaceable away from said valve seat to permit flow from said ventricular catheter into said chamber;

a rotor journaled in said chamber for rotation about the axis of said chamber;

a spring blade fixed to said rotor, extending arcuately along said wall, bearing deflectably outwardly against said valve member and sliding thereon to bias said valve member against said valve seat with a force which is a function of the angular position of said rotor in said chamber, the improvement wherein said rotor is a disk in the form of a circular sector extending over about at least 180° and having a peripheral surface and two radial end surfaces, and stop means extending from said bottom wall of said chamber between said radial end surfaces of said rotor.

2. The valve defined in claim 1 wherein said rotor is a disk in the form of a circular sector extending over about 270°.

3. The valve defined in claim 1, wherein the spring extends along at least one half of the periphery of said chamber and is fixed to said peripheral surface of said rotor adjacent to one of the radial surfaces thereof.

* * * * *